(12) United States Patent
Mishra

(10) Patent No.: US 12,064,231 B2
(45) Date of Patent: Aug. 20, 2024

(54) ACCESSORY DETECTION IN CAPNOGRAPHY MODULES

(71) Applicant: KONINKLIJKE PHILIPS N.V., Eindhoven (NL)

(72) Inventor: Ashish Mishra, New Britain, CT (US)

(73) Assignee: Koninklijke Philips N.V., Eindhoven (NL)

( * ) Notice: Subject to any disclaimer, the term of this patent is extended or adjusted under 35 U.S.C. 154(b) by 627 days.

(21) Appl. No.: 16/979,368

(22) PCT Filed: Apr. 25, 2019

(86) PCT No.: PCT/EP2019/060576
§ 371 (c)(1),
(2) Date: Sep. 9, 2020

(87) PCT Pub. No.: WO2019/211152
PCT Pub. Date: Nov. 7, 2019

(65) Prior Publication Data
US 2021/0038114 A1   Feb. 11, 2021

Related U.S. Application Data

(60) Provisional application No. 62/664,563, filed on Apr. 30, 2018.

(51) Int. Cl.
*A61B 5/08* (2006.01)
*A61B 5/083* (2006.01)
(Continued)

(52) U.S. Cl.
CPC ............ *A61B 5/082* (2013.01); *A61B 5/0836* (2013.01); *A61M 16/085* (2014.02);
(Continued)

(58) Field of Classification Search
CPC ........... A61B 5/08; A61B 5/087; A61B 5/082; A61B 5/0836; A61B 5/097;
(Continued)

(56) References Cited

U.S. PATENT DOCUMENTS 4,168,394 A * 9/1979 Yuey .................... G21C 17/116
277/318
6,089,105 A   7/2000 Ricciardelli
(Continued)

FOREIGN PATENT DOCUMENTS

AU   2015201694 A1   4/2015
GB      2421444 A *  6/2006 ........ A61M 16/0051
(Continued)

OTHER PUBLICATIONS

International Search Report for PCT/EP2019/060576 filed Apr. 25, 2019.

*Primary Examiner* — Yi-Shan Yang
*Assistant Examiner* — Jonathan E. Cooper
(74) *Attorney, Agent, or Firm* — Daniel H. Brean

(57) ABSTRACT

A respiratory gas flow coupling includes a device connector having a female receptacle or male nipple with a side-oriented leak path. A patient accessory connector has a male nipple or female receptacle adapted to connect with the female receptacle or male nipple of the device connector. The patient accessory connector seals the side-oriented leak path of the female receptacle or male nipple of the device connector when the patient accessory connector is connected with the device connector. The side-oriented leak path is disposed at a position such that a shorter male nipple or female receptacle of an incompatible patient accessory connector which is shorter than the male nipple of the patient accessory connector does not seal the side-oriented leak path when the incompatible patient accessory connector with the shorter male nipple is connected with the device connector.

9 Claims, 10 Drawing Sheets

(51) Int. Cl.
*A61M 16/00* (2006.01)
*A61M 16/08* (2006.01)

(52) U.S. Cl.
CPC ............... *A61M 2016/003* (2013.01); *A61M 2202/0225* (2013.01); *A61M 2205/50* (2013.01)

(58) Field of Classification Search
CPC ..... A61B 2010/0087; A61B 2562/225; A61M 2205/6018; A61M 2205/60; A61M 16/085; A61M 2016/003; A61M 2202/0225; A61M 2205/50; A61M 2016/0027; A61M 2205/183; A61M 2039/205; F16L 2201/10; G01N 33/497
USPC .............. 137/513, 513.3; 277/320, 602–625; 285/13, 14
See application file for complete search history.

(56) References Cited

U.S. PATENT DOCUMENTS

| | | | | |
|---|---|---|---|---|
| 6,371,209 | B1* | 4/2002 | Allyn | E21B 31/107 173/90 |
| 7,416,223 | B1* | 8/2008 | Sulmone | F16L 15/008 285/391 |
| 9,579,498 | B2* | 2/2017 | Colman | A61M 39/10 |
| 11,246,506 | B2 | 2/2022 | Gunneson | |
| 2004/0147901 | A1* | 7/2004 | Py | A61M 5/2033 604/176 |
| 2005/0137491 | A1* | 6/2005 | Paz | A61B 5/0878 600/543 |
| 2008/0200903 | A1* | 8/2008 | Christensen | A61M 39/20 604/537 |
| 2010/0071693 | A1* | 3/2010 | Allum | A61M 16/0833 128/205.24 |
| 2010/0090456 | A1* | 4/2010 | Halaczkiewicz | F16L 19/0212 285/12 |
| 2011/0237969 | A1 | 9/2011 | Eckerbom et al. | |
| 2012/0285464 | A1* | 11/2012 | Birch | A61M 16/0438 128/205.25 |
| 2014/0180138 | A1* | 6/2014 | Freeman | A61B 5/0809 600/536 |
| 2017/0224975 | A1 | 8/2017 | Erlich et al. | |
| 2017/0239432 | A1* | 8/2017 | Delangre | G16H 20/40 |
| 2018/0043125 | A1 | 2/2018 | Bencke et al. | |
| 2018/0235512 | A1* | 8/2018 | Gunneson | A61B 5/0836 |
| 2018/0344209 | A1* | 12/2018 | Higgins, Jr. | A61B 5/091 |
| 2019/0224079 | A1* | 7/2019 | Davis | A61J 15/0096 |
| 2019/0290960 | A1* | 9/2019 | Rettig, Jr. | A63B 23/18 |

FOREIGN PATENT DOCUMENTS

| | | | | |
|---|---|---|---|---|
| GB | 2421444 B | 6/2006 | | |
| JP | 2016016008 A | 2/2016 | | |
| WO | WO-2004037335 A1 * | 5/2004 | ............ | A61M 39/10 |
| WO | WO-2014163850 A1 * | 10/2014 | ............ | A61M 39/10 |

* cited by examiner

ACCESSORY DETECTION IN CAPNOGRAPHY MODULES

CROSS-REFERENCE TO PRIOR APPLICATIONS

This application claims the priority benefit under 35 U.S.C. § 371 of International Patent Application No. PCT/EP2019/060576, filed on Apr. 25, 2019, which claims the priority benefit of U.S. Provisional Patent Application No. 62/664,563, filed on Apr. 30, 2018, the contents of which are herein incorporated by reference.

FIELD

The following relates generally to capnography or other respiratory gas monitoring devices, to patient respiratory monitoring, to nasal cannula or other patient accessories for patient respiratory monitoring, and to like applications.

BACKGROUND

In capnography, the carbon dioxide ($CO_2$) content of respiratory gases are sampled, e.g. using a sidestream flow path tapped off the expiration flow of a mechanical respirator. A common approach is to formulate the capnography data as the end-tidal $CO_2$ (et$CO_2$) vital sign, or as its partial pressure equivalent (PET$CO_2$). The capnography data may be otherwise processed and/or utilized—for example, the capnography waveform plotting $CO_2$ as a function of time (or alternatively against expired volume) can be interpreted by skilled medical professionals to provide information such as breathing rate or period, information about gas exchange in the lungs, information about the efficacy of mechanical ventilation, or so forth. While a common diagnostic in the context of mechanically ventilated patients, capnography also finds application in respiratory monitoring of non-ventilated patients. Moreover, while capnography is a common respiratory gas analyzer in clinical settings, other respiratory gas analyzers are sometimes used, for example to track oxygen content of respired gases.

Reliability of capnography or another respiratory gas analyzer is dependent upon the connection with the patient. In a sidestream configuration, respired gas is drawn from expired gas exiting via the patient's nose or mouth or an endotracheal tube. The capnography includes an air pump to draw respired gas through the $CO_2$ sampling cell. (In an alternative mainstream configuration, the $CO_2$ sampling cell is in-line with the respiratory circuit). The sidestream configuration has certain advantages, but relies upon a patient accessory to provide the flow path for respired gas into the capnograph. The patient accessory may, for example, be a nasal cannula, a T-connection into the expiration tubing of a ventilator flow circuit, or so forth. The patient accessory should have appropriate flow resistance, tubing length, or other characteristics in order to ensure accuracy of the $CO_2$ measurements. In practice, however, it is sometimes the case that a non-standard patient accessory may be connected with the capnography, leading to unreliable capnography measurements and potential clinical misinterpretation. Naturally, if a patient accessory is not connected at all, then $CO_2$ measurements are wholly invalid.

The following discloses certain improvements.

SUMMARY

In some embodiments disclosed herein, a respiratory gas flow coupling comprises: a device connector having a female receptacle or male nipple wherein the female receptacle or male nipple of the device connector includes a side-oriented leak path; and a patient accessory connector having a male nipple or female receptacle adapted to connect with the female receptacle or male nipple of the device connector. The patient accessory connector seals the side-oriented leak path of the female receptacle or male nipple of the device connector when the patient accessory connector is connected with the device connector. The side-oriented leak path is disposed at a position along the female receptacle such that a shorter male nipple of an incompatible patient accessory connector which is shorter than the male nipple of the patient accessory connector does not seal the side-oriented leak path when the incompatible patient accessory connector with the shorter male nipple is connected with the device connector.

In some embodiments disclosed herein, a respiratory gas analyzer comprises: a device connector having a female receptacle or male nipple wherein the female receptacle or male nipple includes a side-oriented leak path and wherein the female receptacle or male nipple is adapted to connect with an associated patient accessory connector with the connected associated patient accessory connector sealing the side-oriented leak path; a respiratory gas measurement cell; and a pump operatively connected to draw air flow from the device connector and from the side-oriented leak path through the respiratory gas measurement cell.

In some embodiments disclosed herein, a respiratory gas analysis method comprises: connecting a patient accessory with a respiratory gas analyzer using a patient accessory connector of the patient accessory and a device connector of the respiratory gas analyzer wherein the device connector has a side-oriented leak path that is sealed by connection of the patient accessory connector with the device connector; operating a pump to draw air flow from the patient accessory into the respiratory gas analyzer via the connected patient accessory connector and device connector; detecting whether the patient accessory is connected with the respiratory gas analyzer based on measurement of the air flow; and using the respiratory gas analyzer, performing respiratory gas analysis on the drawn air flow conditional upon the patient accessory being detected as connected with the respiratory gas analyzer.

One advantage resides in providing for detection of an operational connection of a patient accessory with a capnograph or other respiratory gas analyzer.

Another advantage resides in providing for detection of an operational connection of a patient accessory of a recommended type with a capnograph or other respiratory gas analyzer.

Another advantage resides in providing for detection of a gas-tight connection of a patient accessory with a capnograph or other respiratory gas analyzer.

Another advantage resides in providing for detection of the type of patient accessory connected with a capnograph or other respiratory gas analyzer.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
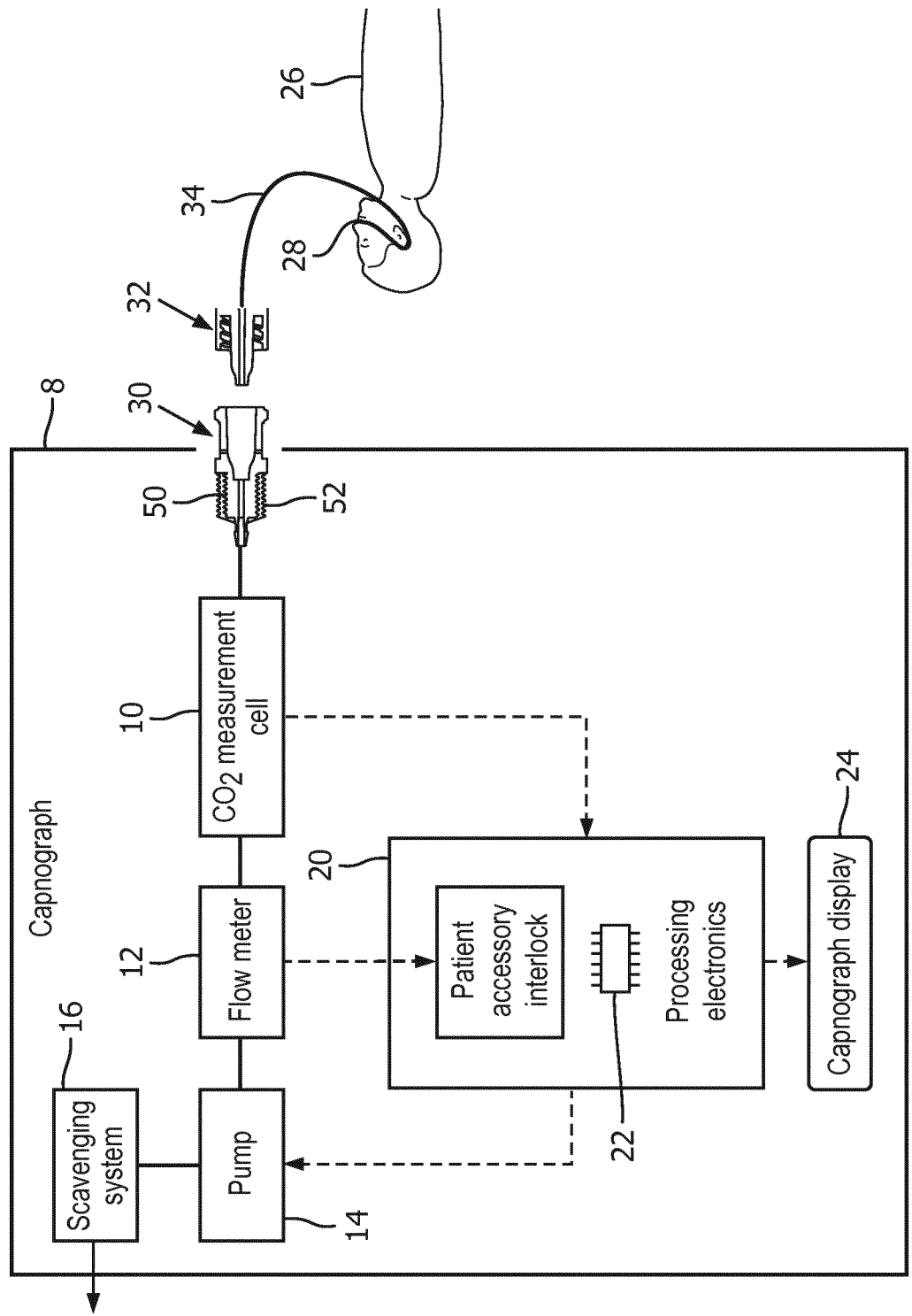
FIG. 1 diagrammatically illustrates a capnograph and an associated patient accessory.

With reference to FIG. 1, a respiratory gas analyzer 8 includes a gas flow path comprising a respiratory gas measurement cell 10, a flow meter 12, a pump 14, and a scavenging system 16. The respiratory gas measurement cell 10 is designed to detect and measure one or more respiratory gases. In the illustrative example, the respiratory gas analyzer 8 is a capnograph 8 and the respiratory gas measurement cell 10 is designed to detect and measure carbon dioxide ($CO_2$) concentration or partial pressure in respiratory gas flowing through the $CO_2$ measurement cell 10. The $CO_2$ may, for example, be measured optically by measuring transmission of a narrow-band light at a wavelength (e.g. in the infrared) of strong absorption by $CO_2$, typically corrected for absorption by nitrous oxide in the respiratory gas. The light source emits light over a spectrum that encompasses the desired measurement band (e.g. 4.26 micron in some embodiments). The light may extend spectrally beyond the detection spectral range if suitable spectral filtering is employed. In some embodiments the light source may include an optical chopper, pulsed power supply, or the like in order to deliver the emitted light as light pulses. By way of another illustrative example, the respiratory gas measurement cell may measure partial pressure or concentration of oxygen in the respiratory gas, or so forth. The pump 14 draws respiratory gas through the measurement cell 10, while the flow meter 12 measures the flow. The flow meter 12 may use any flow measurement technique applicable for respiratory air, and may optionally take the form of a differential pressure meter, flow resistance meter, or so forth. The scavenging system 16 is optional but typically employed in a medical setting in which the patient may be administered an inhaled anesthetic or analgesic agent or inhaled medication—the scavenging system 16 scrubs or removes these from the air flow prior to discharge. The capnograph or other respiratory gas analyzer typically further includes processing electronics 20, e.g. implemented as a microprocessor or microcontroller 22 programmed to execute instructions stored in an EEPROM, ROM, or other memory (not shown) to read $CO_2$ or other gas measurements from the measurement cell 10 and process these measurements to generate clinical data such as the capnograph waveform, $etCO_2$ or $PETCO_2$ values, and/or so forth. The patient respiratory gas data may be displayed on a built-in display 24, and/or may be transmitted via a wired and/or wireless electronic data network to a bedside patient monitor, nurses' station, Electronic Medical or Health Record (EMR or EHR), and/or so forth.

Figure 2:
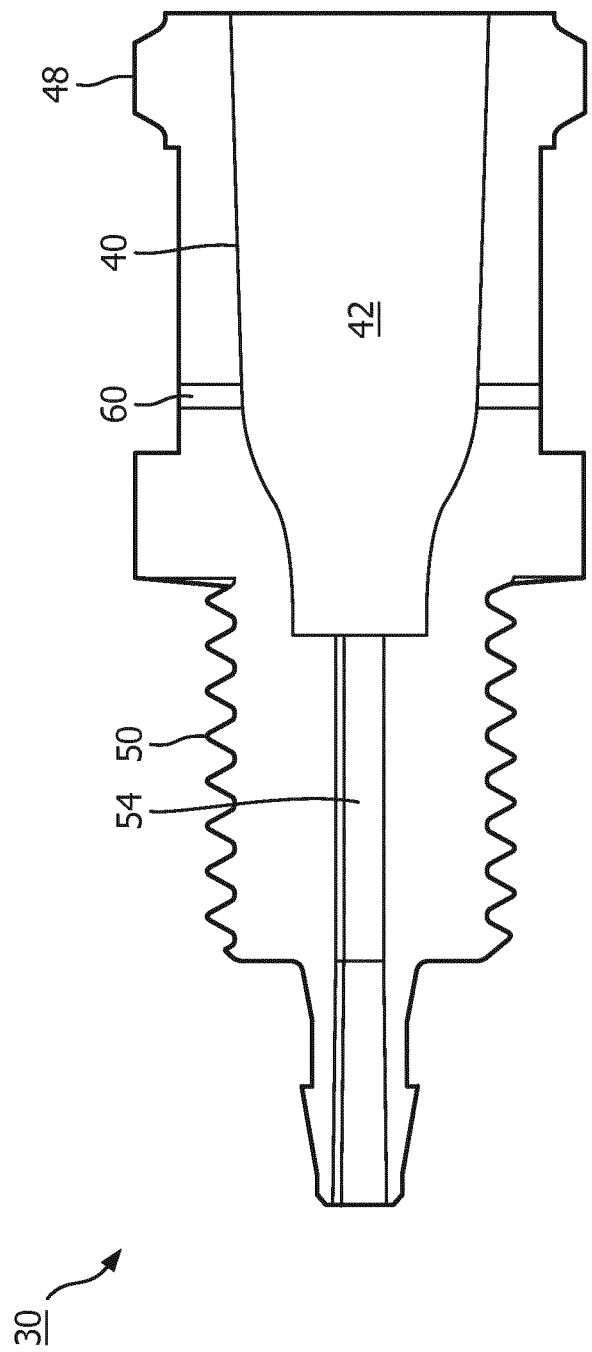
FIG. 2 diagrammatically shows the female connector of the capnograph of FIG. 1.
Figure 3:
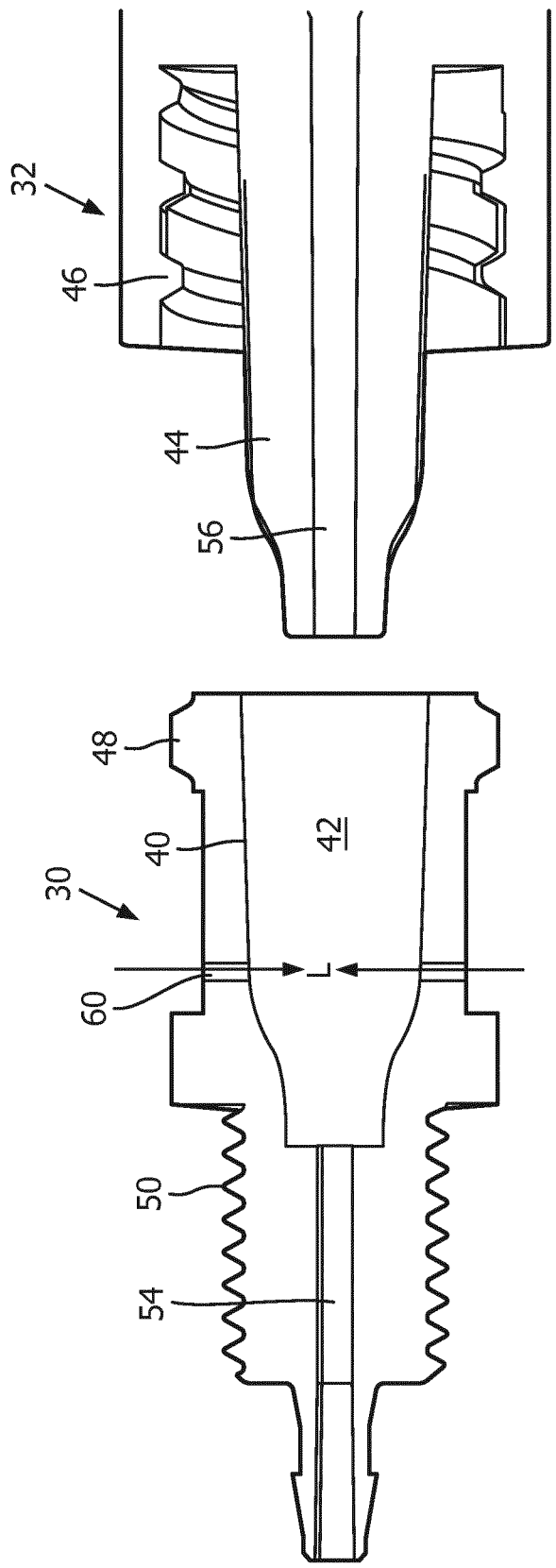
FIG. 3 diagrammatically shows the female connector of the capnograph and male connector of the patient accessory of FIG. 1, before connecting together.
Figure 4:
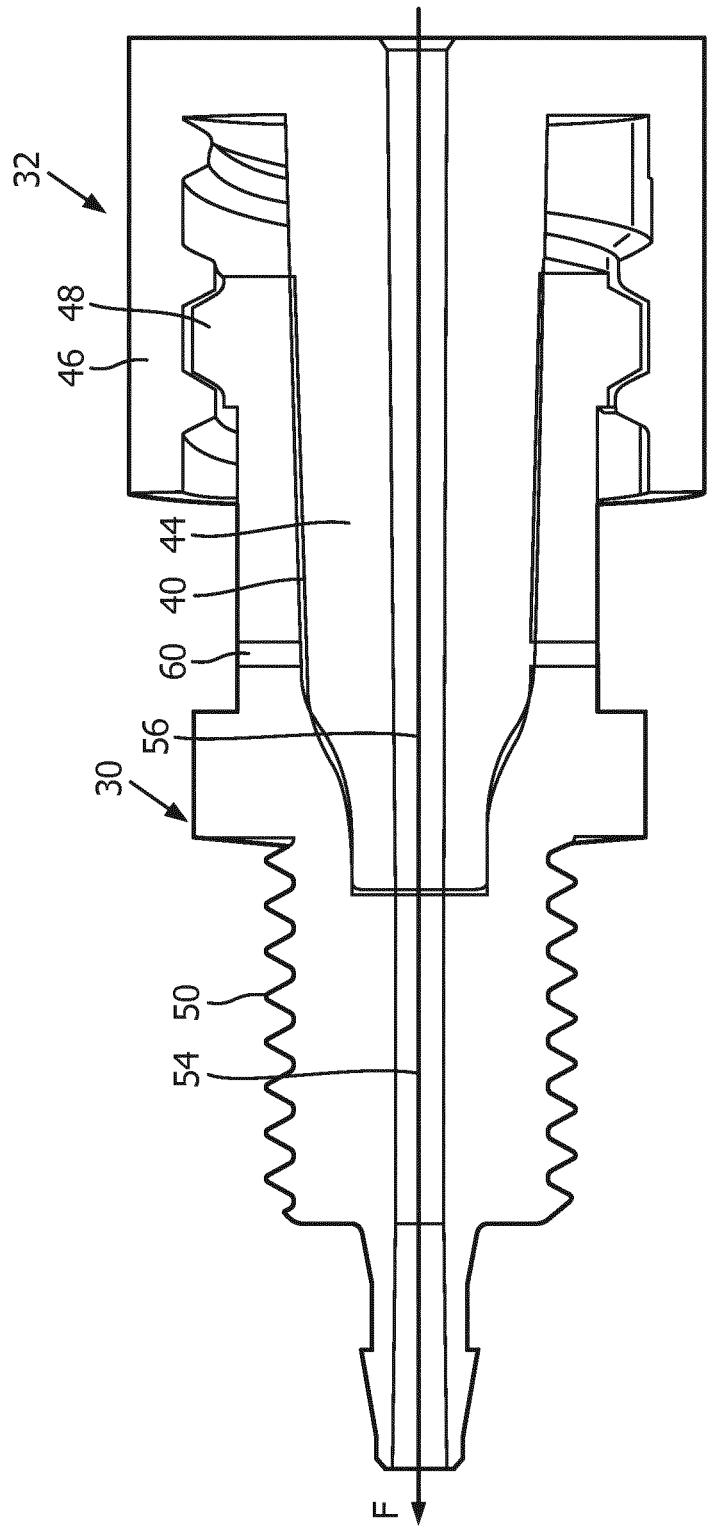
FIG. 4 diagrammatically shows the female connector of the capnograph and male connector of the patient accessory of FIG. 1, connected together.

With continuing reference to FIG. 1 and with further reference to FIGS. 2-4, respiratory gas expired by a patient 26 is input to the respiratory gas analyzer 8 by way of a patient accessory 28, for example an illustrative nasal cannula 28, or a T-connection to a mechanical ventilator circuit or to an endotracheal tube, or so forth. To connect the patient accessory 28 with the respiratory gas analyzer 8, a device connector 30 is provided on or connected with the respiratory gas analyzer 8, and a mating patient accessory connector 32 is provided at the distal end of respiratory gas tubing 34 of the patient accessory 28. The two connectors 30, 32 form a mating male/female pair, in which one connector has a female receptacle and the other connector has a male nozzle that fits into the female receptacle. Specifically, in the illustrative embodiment of FIGS. 2-4, the device connector 30 has a female receptacle 40 with a lumen 42; while, the illustrative mating patient accessory connector 32 has a male nipple 44 sized and shaped to fit into the female receptacle 40 as best seen in FIG. 3 (before connection) and FIG. 4 (after connection). The connection may employ various securing mechanisms, such as a friction fit, a threaded engagement, or so forth. In the illustrative example of FIGS. 2-4, the securing mechanism is a threaded engagement in which an outer threaded collar 46 of the patient accessory connector 32 engages a nub or ring or outer threading 48 on an outer surface of the device connector 30. In the illustrative example of FIGS. 2-4, the device connector 30 further includes a mounting threading 50 that, as diagrammatically indicated in FIG. 1, enables the device connector 30 to be threaded into a mating threaded mounting opening 52 of the capnograph 8. However, other arrangements are contemplated; as another example, the capnograph may include a length of gas tubing extending away from the capnograph and terminating in the device connector. In another contemplated variation, it is contemplated for the device connector to be integral with the $CO_2$ measurement cell so as to form a modular $CO_2$ sampling cell cartridge.

As best seen in FIGS. 2 and 3, the device connector 30 includes a flow path 54 in fluid communication with the lumen 42 of the female receptacle 40; while, the patient accessory connector 32 includes a flow path 56 passing through the male nipple 44. As best seen in FIGS. 1 and 4, when the two connectors 30, 32 are connected together these flow paths 54, 56 are in fluid communication to allow respiratory gas to flow from the tubing 34 of the patient accessory 28 through the nipple 44 via the flow path 56 and thence into and through the device connector 30 via the flow path 54 and thence into the $CO_2$ measurement cell 10. FIG. 4 shows an arrow F indicating the direction of air flow through the flow path 56 passing through the male nipple 44 and thence through the flow path 54 passing through the device connector 30. As previously noted, in the illustrative sidestream configuration this respiratory gas flow F is drawn by operation of the pump 14, although positive pressure exerted by the patient and/or by operation of a mechanical ventilator may also drive this respiratory gas flow during the exhalation phase of the breathing cycle. (It is possible that negative pressure from the patient and/or mechanical ventilator may slow or wholly interrupt the respiratory gas flow during the inhalation phase).

With continuing reference to FIGS. 1-4, the female receptacle 40 of the device connector 30 includes a side-oriented leak path 60. As illustrated, the side-oriented leak path 60 comprises a passage passing through a wall of the female receptacle 40. The passage has a first open end in fluid communication with the lumen 42 of the female receptacle 40 and a second open end in fluid communication with ambient air. When the patient accessory connector 32 is not connected with the device connector 30 (FIG. 3), air flow through the flow path 54 includes a leakage contribution L flowing into the lumen 42 of the receptacle 40 of the device connector 30. This leakage flow contribution L contributes to flow through the flow path 54 under the pull of the pump 14. As seen in FIG. 4, the patient accessory connector 32 seals the side-oriented leak path 60 of the female receptacle 40 of the device connector 30 when the patient accessory connector 32 is connected with the device connector 30.

Thus, an approach for detecting whether the patient accessory connector 32 is connected with the device connector 30 (so that the patient accessory 28 is operatively connected with the capnograph 8) is apparent. If constant leakage flow is observed in response to running the pump 14, then the patient accessory connector 32 is not connected with the device connector 30. This leakage flow includes the leakage flow L coming through the side-oriented leak path 60, as well as leakage flow coming in from the open end of the lumen 42 of the device connector 30.

On the other hand, if the patient accessory connector 32 is connected with the device connector 30 then there should be time intervals over which little or no leakage flow is observed. These intervals would be during inhalation when there is no in-flow of gas into the flow path 56 passing through the male nipple 44 of the patient accessory connector 32.

However, considering FIGS. 3-4 alone, it is not apparent that the side-oriented leak path 60 serves a useful purpose. This is because if the patient accessory connector 32 is not connected with the device connector 30 then leakage flow will be present coming in from the open end of the lumen 42 of the device connector 30. Moreover, this leakage flow from the open end of the lumen 42 is expected to be larger than the leakage flow L coming in via the side-oriented leak path 60 simply because of the larger orifice of the open end of the lumen 42.

Figure 5:
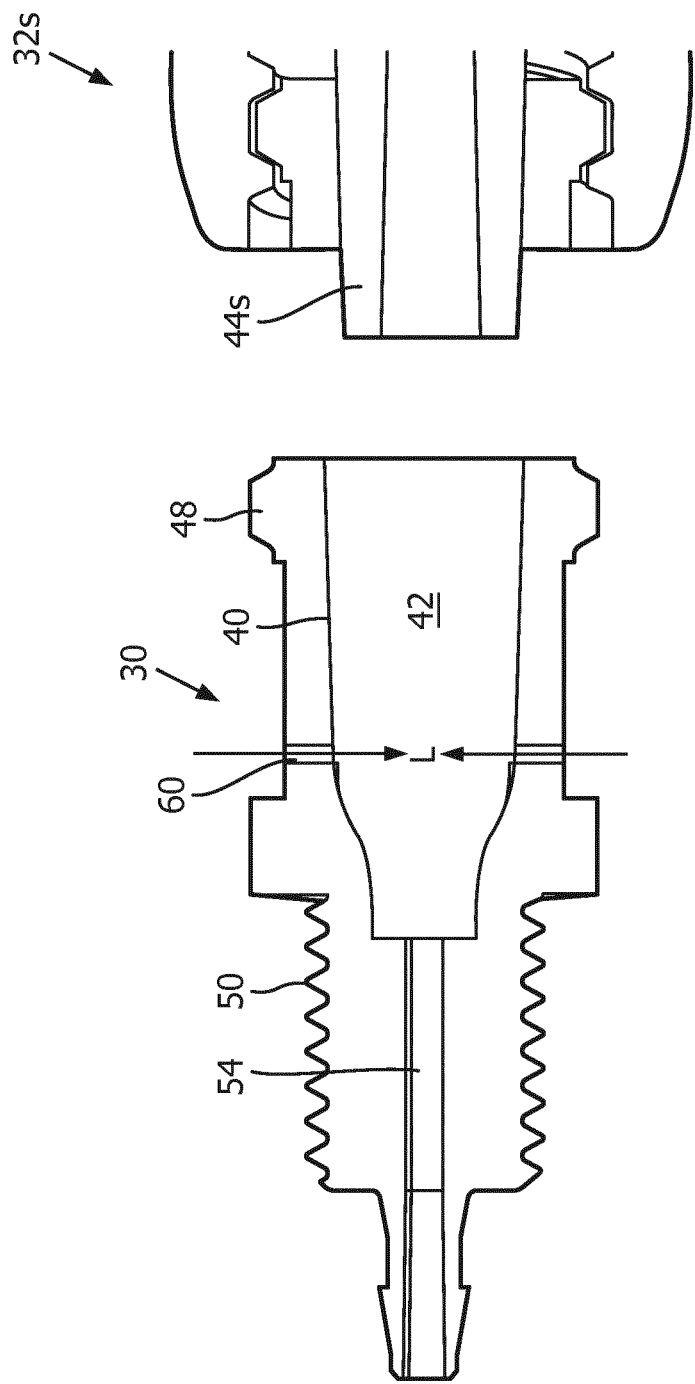
FIG. 5 diagrammatically shows the female connector of the capnograph of FIG. 1 and the male connector of an compatible patient accessory, before connecting together.
Figure 6:
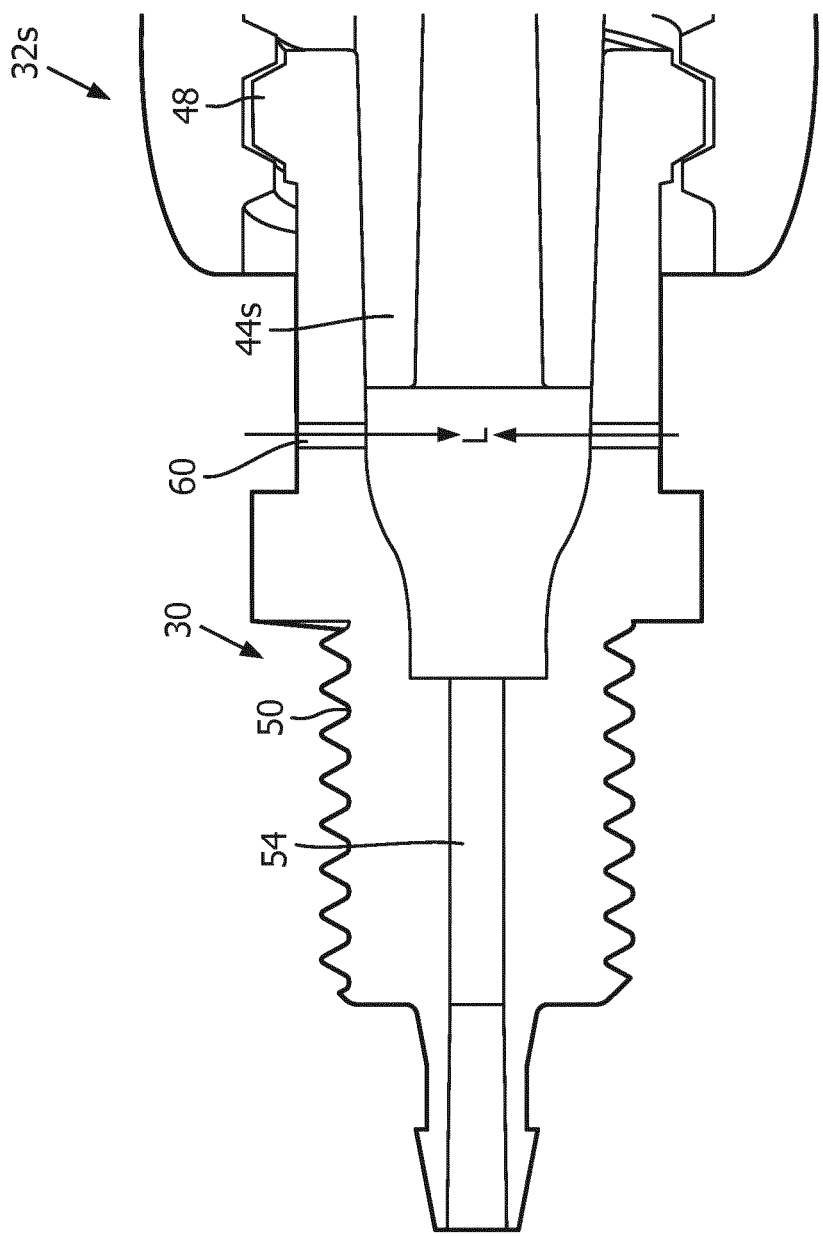
FIG. 6 diagrammatically shows the female connector of the capnograph of FIG. 1 and the male connector of the compatible patient accessory of FIG. 5, connected together.

With reference now to FIGS. 5 and 6, a purpose of the side-oriented leak path 60 is illustrated. In this example, the patient accessory connector 32 which is associated with the device connector 30 is replaced by a different patient accessory connector 32s which has a shorter nipple 44s compared with the nipple 44 of the associated patient accessory connector 32. FIG. 5 shows the device connector 30 and the shorter-nipple patient accessory connector 32s before connection; FIG. 6 shows the connectors 30, 32s after connection. As seen in FIG. 6, due to the shorter nipple 44s, the patient accessory connector 32s fails to seal the side-oriented leak path 60 of the device connector 30. Thus, even when the two connectors 30, 32s are connected as shown in FIG. 6, the leakage flow L will be present as indicated in FIG. 6, although leakage through the open end of the lumen 42 of the device connector 30 is now blocked by the connected patient accessory connector 32s. Thus, the side-oriented leak path 60 can be used to detect whether the correct (e.g. associated) patient accessory connector 32 is connected as shown in FIG. 4, or if instead an incorrect patient accessory connector 32s with a shorter nipple 44s is connected.

By way of non-limiting illustration, in one embodiment the capnograph 8 is designed to operate with a flow of 50±10 ml/min when connected with the proper accessory (e.g. as shown in FIG. 4). Thus, a flow of greater than 60 ml/min will be detected as a leak. Accordingly, the side-oriented leak path 60 should have a sufficiently large aperture to introduce leakage of 10 ml/min in the case of FIG. 6 when running with the pump set to draw a flow of 50 ml/min with the correct connector (shown in FIG. 4).

It will be appreciated that the flow measurements can alternatively be measured and processed as cell pressure measurements. In the aforementioned non-limiting illustrative example, the capnograph 8 is designed to operate with a cell pressure of −3±5 mmHg when connected with the proper accessory (e.g. as shown in FIG. 4). Thus, a flow measured as a pressure of less than +2 mmHg will be detected as a leak.

Figure 7:
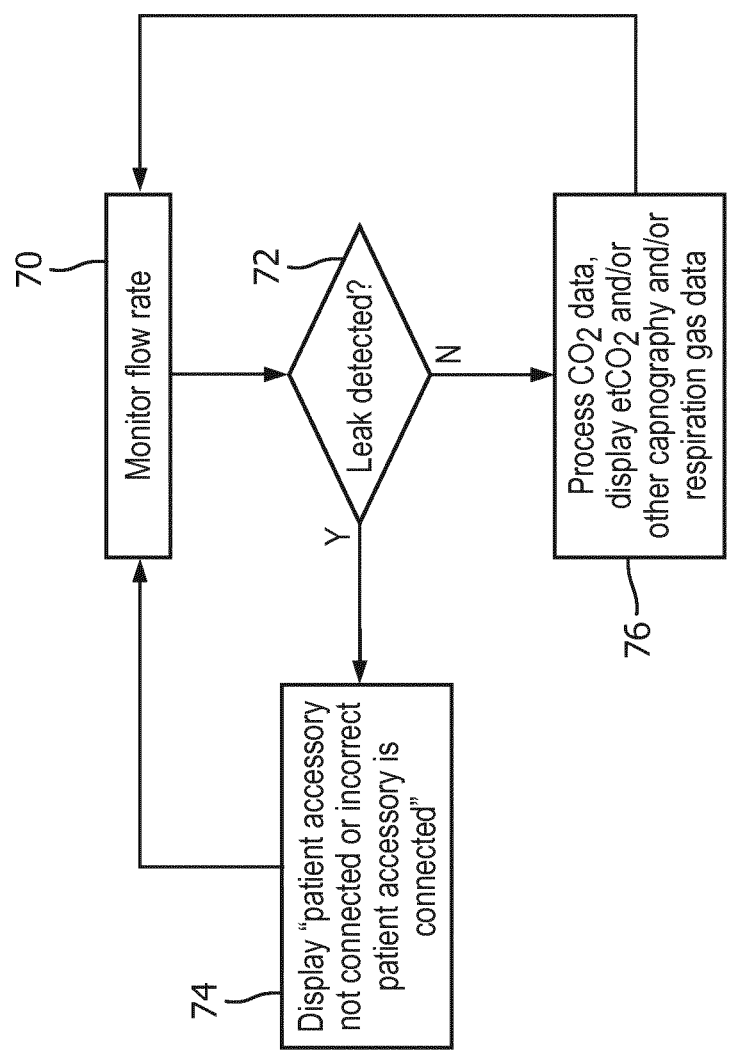
FIG. 7 flowcharts a suitable operation of the patient accessory interlock of the capnograph of FIG. 1.

With reference back to FIG. 1 and with further reference to FIG. 7, an operational sequence suitably performed by the capnograph 8 of FIG. 1 is shown. In an operation 70, the flow rate is monitored as a function of time using the flow meter 12. In an operation 72, the processing electronics 20 are programmed to determine whether a leak is detected. This can be done in various ways. A leak generally cannot be detected simply by detecting flow rate greater than some threshold, since even if the connectors 30, 32 are connected together with the side-oriented leak path 60 blocked by the nipple 44 of the patient accessory 32, high flow rate may be measured during exhalation. In one approach, the leak detection operation 72 monitors the flow rate over a time period long enough to encompass at least one breath, and the minimum air flow rate detected over this time period is used to assess whether a leak is detected. If the connectors 30, 32 are connected together with the side-oriented leak path 60 blocked by the nipple 44 of the patient accessory 32, then the minimum air flow rate will occur during inhalation at which time the flow rate will be substantially reduced or even zero. On the other hand, if the connectors 30, 32 are disconnected then the minimum air flow rate will be high since leakage will occur both through the open end of the lumen 42 of the device connector 30 and through the side-oriented leak path 60. Finally, if the incompatible patient accessory connector 32s with a shorter nipple 44s is connected with the device connector 30 then the minimum air flow rate will be intermediate since leakage will occur only through the side-oriented leak path 60 but not through the open end of the lumen 42 of the device connector 30. In the example of FIG. 7, if the minimum air flow rate is at or above the intermediate level corresponding to the incompatible patient accessory connector 32s being connected, then a notice: "patient accessory not connected or incorrect patient accessory is connected" 74 is displayed on the display 24. On the other hand, if the operation 72 detects no leak (that is, the minimum air flow rate is below the intermediate level corresponding to connection of the incorrect patient accessory connector 32s) then flow passes to operation 76 at which the processing electronics 20 are programmed to process $CO_2$ data measured by the $CO_2$ measurement cell 10 and displaying the $etCO_2$ and/or other capnography data (and/or other respiratory gas data in the case of a respiratory gas monitor that monitors oxygen or some other respiratory gas besides $CO_2$).

In an alternative embodiment of the operations 72, 74, different messages are displayed depending upon the situation. For example, "patient accessory not connected" may be displayed if the minimum air flow rate is at or above the high leak rate corresponding to a disconnection; whereas, "incorrect patient accessory is connected" is displayed if the minimum air flow rate is at or above the intermediate level corresponding to connection of the incorrect patient accessory connector 32s but below the high leak rate corresponding to a disconnection.

In a further variant, if the minimum air flow rate is at or above the intermediate level corresponding to connection of the incorrect patient accessory connector 32s but below the high leak rate corresponding to a disconnection, then processing may transfer to operation 76 to process $CO_2$ measurements, taking into account that the patient accessory connector 32s with short nipple 44s is connected. For example, the patient accessory connector 32 may be provided in conjunction with a patient accessory that connects into the breathing circuit or tees off an endotracheal tube, while the patient accessory connector 32s may be provided in conjunction with a patient accessory comprising a nasal cannula. In this case, $CO_2$ measurements made using a patient accessory having the patient accessory connector 32 may be deemed more reliable due to the airtight connection into the breathing circuit or endotracheal tube, whereas $CO_2$ measurements made using a patient accessory (here nasal cannula) having the patient accessory connector 32s may be deemed less reliable due to the potentially leaky connection provided by the nasal cannula. In these embodiments, $CO_2$ data processing should take into account the leakage air flow L through the side-oriented leak path 60, e.g. by scaling the $etCO_2$ upward to account for the negligible $CO_2$ level in the leak air flow component.

It is noteworthy that the cross-sectional area of the side-oriented leak path 60 can be optimized to control the difference between the intermediate level leakage through the leak path 60 only (when the incorrect patient accessory connector 32s is connected) compared with the high leakage through both the leak path 60 and the open end of the lumen 42 (when no patient accessory connector is connected with the device connector 30). Likewise, the magnitude of the leakage flow L can be tailored by optimizing the cross-sectional area of the side-oriented leak path 60, e.g. to allow for this leakage flow L to be accurately accounted for when using a patient accessory connector 32s that does not block the leakage flow L.

Figure 8:
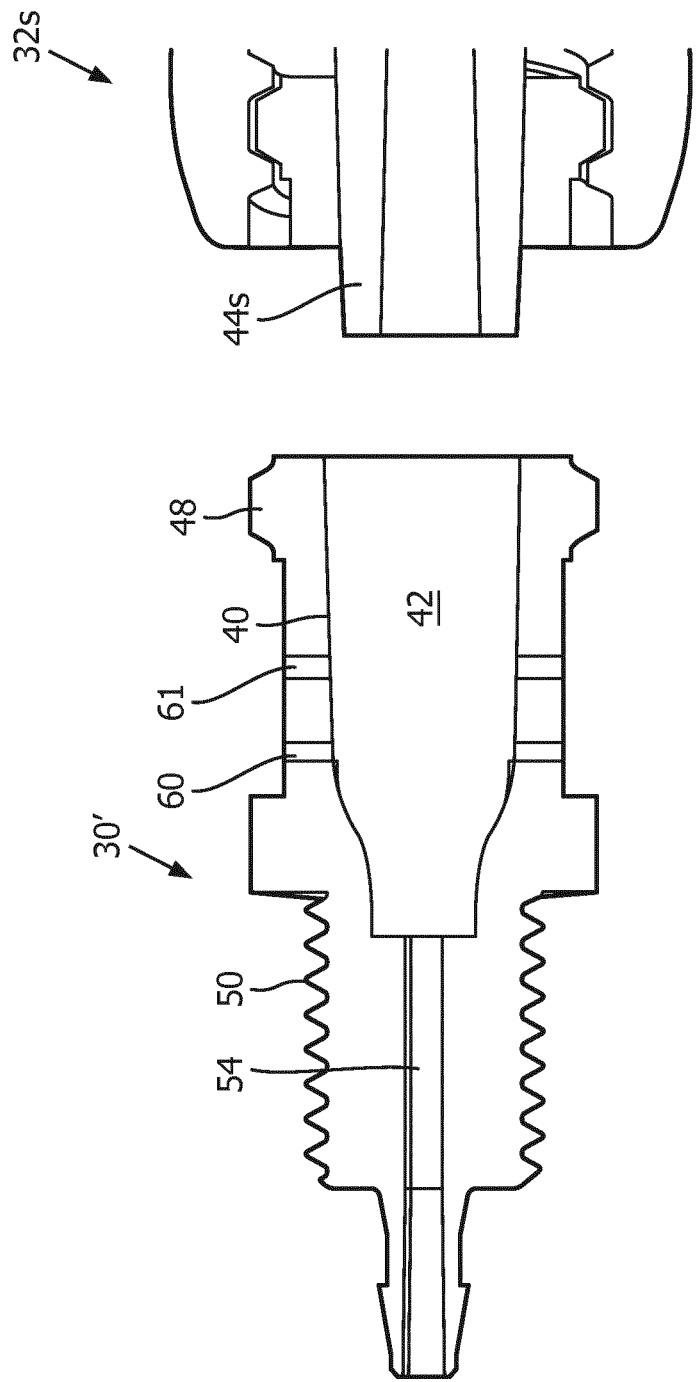
FIG. 8 diagrammatically shows the female connector of the capnograph of FIG. 1 and the male connector of a compatible patient accessory of a particular type, before connecting together.
Figure 9:
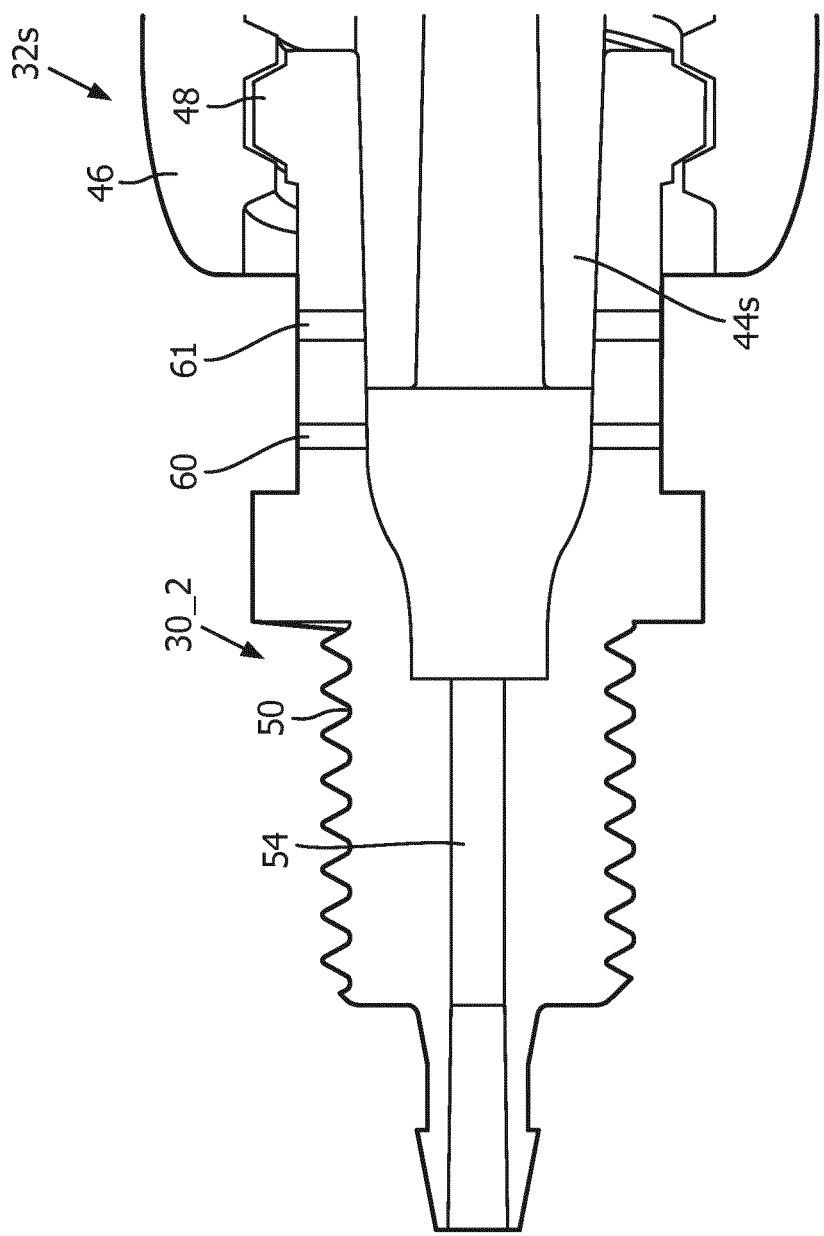
FIG. 9 diagrammatically shows the female connector of the capnograph of FIG. 1 and the male connector of the compatible patient accessory of the particular type of FIG. 8, connected together.

With reference to FIGS. 8 and 9, as a further extension it is contemplated to have two or more side-oriented leak paths 60, 61 in order to provide further discrimination between different patient accessory connectors. In this example, the modified device connector 30' has the same components as the device connector 30 labeled using like reference numbers. However, the modified device connector 30' has a second side-oriented leak path 61 in addition to the already-described side-oriented leak path 60. Thus, in this embodiment the female receptacle 40 of the device connector 30' includes at least two side-oriented leak paths 60, 61 spaced apart along a direction of air flow through the female receptacle 40. FIG. 8 illustrates the modified device connector 30' prior to connection with the patient accessory connector 32s which has the shorter nipple 44s compared with the nipple 44 of the associated patient accessory connector 32. FIG. 9 illustrates the modified device connector 30' connected with the patient accessory connector 32s with the shorter nipple 44s. As seen in FIG. 9, the shorter nipple 44s blocks the side-oriented leak path 61, but is not long enough to block the side-oriented leak path 60. Thus, intermediate leakage will be observed through the side-oriented leak path 60 but not through the side-oriented leak path 61. On the other hand, if the patient accessory connector 32 with the longer nipple 44 is connected to the modified device connector 30' (connection not illustrated), then both leak paths 60, 61 will be blocked so as to provide the least (or no) leakage. Yet again, if a patient accessory connector with a nipple that is shorter than the nipple 44s of the patient accessory connector 32s is employed (again not shown) then the shortest nipple of such a patient accessory connector may fail to block either of the side-oriented leak paths 60, 61, leading to a higher leakage than the case shown in FIG. 9. In such a way, the multiple side-oriented leak paths 60, 61 designed to be blocked in turn by progressively longer nipples of different patient accessory connector types provides a mechanism for distinguishing, on the basis of the amount of leakage, between the different patient accessory connector types.

In the embodiments described thus far, the device connector 30 is a female connector, that is, has a female receptacle 40, while the patient accessory connector 32 or 32s is a male connector, that is, has a male nipple 44 or 44s that fits into the female receptacle 40. Further, as disclosed herein the female receptacle 40 has a side oriented leak path 60 for detecting connection with a patient accessory connector whose male nipple 44 or 44s is of a certain length. However, it will be appreciated that the "polarity" of the male-female connection may be reversed.

Figure 10:
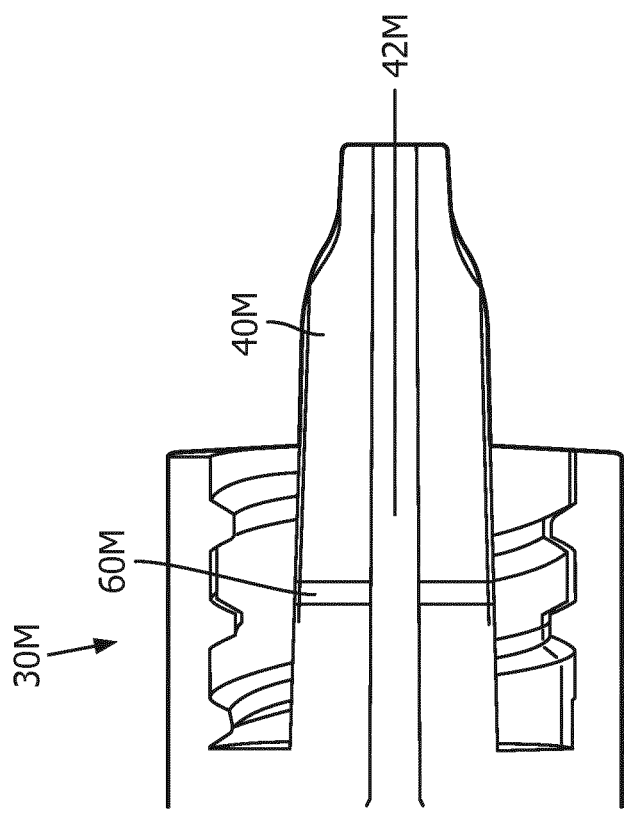
FIG. 10 diagrammatically shows a male embodiment of the device connector.

With reference to FIG. 10, an example of a device connector 30M with a male configuration is shown. The device connector 30M includes a male nipple 40M with a side-oriented leak path 60M. In the embodiment of FIG. 10, the side-oriented leak path 60M comprises a passage passing through a wall of the male nipple 40M, the passage having a first open end in fluid communication with a lumen 42M of the male nipple 40M and a second open end in fluid communication with ambient air. Operation is analogous to the embodiment of FIGS. 2-4 except that in this case a patient accessory connector (not shown) has a female receptacle that mates with the male nipple 40M of the male device connector 30M. If the female receptacle of the patient accessory connector is long enough then it serves to seal the side-oriented leak path 60M; whereas, if the female receptacle of an incorrect patient accessory connector is too short then it will fail to seal the side-oriented leak path 60M. By detecting leakage through the side-oriented leak path 60M analogous to the way described with reference to FIG. 7, it is possible to detect connection of the incorrect (e.g. incompatible) patient accessory connector. Alternatively, analogous to variant embodiments described in conjunction with FIG. 7, such leakage may be used to distinguish between connection of different types of patient accessory connectors and to adjust the respiratory gas analysis in accordance with the type of connected patient accessory.

In a suitable approach, the sealing of the side-oriented leak path 60, 60M is achieved by a plastic-on-plastic seal. For example, considering the embodiment of FIGS. 2-4, the female receptacle 40 of the device connector 30 is plastic, and the male nipple 44 of the patient accessory connector 32 is plastic and (as per FIG. 4) seals the side-oriented leak path 60 of the female receptacle 40 of the device connector 30 by a plastic on plastic seal when the patient accessory connector 32 is connected with the device connector 30.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A respiratory gas flow coupling, comprising:
a device connector of a respiratory gas analyzer having a female receptacle including a side-oriented leak path, the female receptacle having a first longitudinal axis, the side-oriented leak path being oriented substantially orthogonal to the first longitudinal axis; and
a patient accessory connector of a patient accessory having a male nipple adapted to connect with the female receptacle of the device connector, the male nipple-having a second longitudinal axis that is substantially parallel with the first longitudinal axis;
wherein the patient accessory is configured to be connected with the respiratory gas analyzer via the patient accessory connector of the patient accessory and the device connector of the respiratory gas analyzer;
wherein the male nipple of the patient accessory connector seals the side-oriented leak path of the female receptacle of the device connector when the patient accessory connector is connected with the device connector; and
wherein the side-oriented leak path is disposed at a position along the female receptacle such that a shorter male nipple of an incompatible patient accessory connector which is shorter than the male nipple of the patient accessory connector does not seal the side-oriented leak path when the incompatible patient accessory connector with the shorter male nipple is connected with the device connector.

2. The respiratory gas flow coupling of claim 1 wherein the side-oriented leak path comprises a passage passing through a wall of the female receptacle, the passage having a first open end in fluid communication with a lumen of the female receptacle and a second open end in fluid communication with ambient air.

3. The respiratory gas flow coupling of claim 1 wherein:
the female receptacle of the device connector is plastic; and
the male nipple of the patient accessory connector is plastic and seals the side-oriented leak path of the female receptacle of the device connector by a plastic-on-plastic seal when the patient accessory connector is connected with the device connector.

4. The respiratory gas flow coupling of claim 1 wherein:
the female receptacle of the device connector includes at least two side-oriented leak paths spaced apart along a direction of air flow through the female receptacle.

5. A respiratory gas flow coupling, comprising:
a device connector of a respiratory gas analyzer having a male nipple, the male nipple having a first longitudinal axis and a side-oriented leak path through a wall of the male nipple, the side-oriented leak path being oriented substantially orthogonal to the first longitudinal axis and comprising a passage having a first open end in fluid communication with a lumen of the male nipple and a second open end in fluid communication with ambient air; and
a patient accessory connector of a patient accessory having a female receptacle adapted to connect with the male nipple of the device connector, the female receptacle having a second longitudinal axis that is substantially parallel with the first longitudinal axis;
wherein the patient accessory is configured to be connected with the respiratory gas analyzer via the patient accessory connector of the patient accessory and the device connector of the respiratory gas analyzer;
wherein the female receptacle of the patient accessory connector seals the side-oriented leak path of the male nipple of the device connector when the patient accessory connector is connected with the device connector; and
wherein the side-oriented leak path is disposed at a position along the male nipple such that a shorter female receptacle of an incompatible patient accessory connector which is shorter than the female receptacle of the patient accessory connector does not seal the side-oriented leak path when the incompatible patient accessory connector with the shorter female receptacle is connected with the device connector.

6. The respiratory gas flow coupling of claim 5 wherein:
the male nipple of the device connector is plastic; and
the female receptacle of the patient accessory connector is plastic and seals the side-oriented leak path of the male nipple of the device connector by a plastic-on-plastic seal when the patient accessory connector is connected with the device connector.

7. The respiratory gas flow coupling of claim 5 wherein:
the male nipple of the device connector includes at least two side-oriented leak paths spaced apart along a direction of air flow through the male nipple.

8. The respiratory gas analyzer of claim 5 wherein the respiratory gas analyzer comprises a capnograph.

9. A respiratory gas analysis method comprising:
connecting a patient accessory with a respiratory gas analyzer using a patient accessory connector of the patient accessory and a device connector of the respiratory gas analyzer, the device connector having a first longitudinal axis and a female receptacle including a side-oriented leak path comprising a passage passing through a wall of the female receptacle, the passage having a first open end in fluid communication with a lumen of the female receptacle and a second open end in fluid communication with ambient air, the patient accessory connector having a second longitudinal axis that is parallel to the first longitudinal axis and having a male nipple adapted to connect with the female receptacle of the device connector, the side-oriented leak path being oriented substantially orthogonal to the first and second longitudinal axes, wherein the male nipple of the patient accessory connector seals the side-oriented leak path of the female receptacle of the device connector when the patient accessory connector is connected with the device connector, and wherein the side-oriented leak path is disposed at a position along the female receptacle such that a shorter male nipple of an incompatible patient accessory connector which is shorter than the male nipple of the patient accessory connector does not seal the side-oriented leak path when the incompatible patient accessory connector with the shorter male nipple is connected with the device connector;
operating a pump to draw air flow from the patient accessory into the respiratory gas analyzer via the connected patient accessory connector and device connector;
detecting whether the patient accessory is connected with the respiratory gas analyzer based on measurement of the air flow by detecting whether ambient air is flowing through the passage into the lumen of the female receptacle; and using the respiratory gas analyzer, performing respiratory gas analysis on the drawn air flow conditional upon the patient accessory being detected as connected with the respiratory gas analyzer.

\* \* \* \* \*